United States Patent
Walker (10) Patent No.: US 7,089,786 B2
(45) Date of Patent: Aug. 15, 2006

(54) MICROELECTROMECHANICAL SYSTEM AND METHOD FOR DETERMINING TEMPERATURE AND MOISTURE PROFILES WITHIN PHARMACEUTICAL PACKAGING

(75) Inventor: Dwight Sherod Walker, Durham, NC (US)

(73) Assignee: Glaxo Group Limited, Greenford (GB)

( * ) Notice: Subject to any disclaimer, the term of this patent is extended or adjusted under 35 U.S.C. 154(b) by 0 days.

(21) Appl. No.: 10/513,841

(22) PCT Filed: May 12, 2003

(86) PCT No.: PCT/US03/15008

§ 371 (c)(1),
(2), (4) Date: Nov. 5, 2004

(87) PCT Pub. No.: WO03/107397

PCT Pub. Date: Dec. 24, 2003

(65) Prior Publication Data

US 2005/0223827 A1 Oct. 13, 2005

Related U.S. Application Data (60) Provisional application No. 60/380,585, filed on May 15, 2002.

(51) Int. Cl.
*G01B 23/00* (2006.01)
(52) U.S. Cl. ......................................................... 73/73
(58) Field of Classification Search ...................... None
See application file for complete search history.

(56) References Cited

U.S. PATENT DOCUMENTS

| 4,209,955 | A | * | 7/1980 | Seragnoli ........................ 53/54 |
|---|---|---|---|---|
| 4,627,432 | A | | 12/1986 | Newell et al. |
| 4,778,054 | A | | 10/1988 | Newell et al. |
| D299,066 | S | | 12/1988 | Newell et al. |
| 4,811,731 | A | | 3/1989 | Newell et al. |
| D342,994 | S | | 1/1994 | Rand et al. |
| 5,555,707 | A | * | 9/1996 | Schwenger ................... 53/493 |
| 5,590,654 | A | | 1/1997 | Prince |
| 5,739,416 | A | | 4/1998 | Hoenk |
| 5,799,468 | A | * | 9/1998 | Eck et al. ..................... 53/453 |
| 5,837,630 | A | | 11/1998 | Owens et al. |
| 5,860,419 | A | | 1/1999 | Davies et al. |
| 5,917,226 | A | | 6/1999 | Chan et al. |
| 6,032,666 | A | | 3/2000 | Davies et al. |
| 6,128,961 | A | | 10/2000 | Haronian |
| 6,155,423 | A | | 12/2000 | Katzner et al. |
| 6,255,962 | B1 | | 7/2001 | Tanenhaus et al. |
| 6,401,545 | B1 | * | 6/2002 | Monk et al. ................... 73/756 |

(Continued)

OTHER PUBLICATIONS

Jain et al., "Magnetoacoustic remote query temperature and humidity sensors," *Smart Mater. Struct.* 9:502-510 (2000).
Wachter et al., "Micromechanical sensors for chemical and physical measurements," *Rev. Sci. Instrum.* 66(6):3662-3667 (Jun. 1995).

*Primary Examiner*—Robert Raevis
(74) *Attorney, Agent, or Firm*—Robert J. Smith (57) ABSTRACT

A sensor system for determining at least one environmental condition within pharmaceutical packaging comprising a base sheet with at least one pocket formed therein, a lid sheet having a pocket portion, the pocket portion being disposed proximate the pocket when the lid sheet is bonded to the base sheet; and a microelectromechanical (MEMS) sensor disposed proximate the pocket portion.

5 Claims, 4 Drawing Sheets

U.S. PATENT DOCUMENTS

| | | | |
|---|---|---|---|
| 6,757,637 B1 * | 6/2004 | Mertens et al. | 702/156 |
| 2002/0017996 A1 * | 2/2002 | Niemiec | 340/573.1 |
| 2003/0037616 A1 * | 2/2003 | Vikhagen | 73/643 |
| 2003/0055360 A1 * | 3/2003 | Zeleznik et. al. | 600/587 |
| 2003/0088371 A1 * | 5/2003 | Parker | 702/36 |
| 2003/0125774 A1 * | 7/2003 | Salo | 607/21 |

* cited by examiner

MICROELECTROMECHANICAL SYSTEM AND METHOD FOR DETERMINING TEMPERATURE AND MOISTURE PROFILES WITHIN PHARMACEUTICAL PACKAGING

CROSS-REFERENCE TO RELATED APPLICATIONS

This application is filed under 35 U.S.C. § 371 as the United States National Phase Application of International Application No. PCT/US03/15008 filed May 12, 2003 claiming priority from U.S. Application Ser. No. 60/380,585 filed May 15, 2002.

FIELD OF THE INVENTION

The present invention is directed to devices and systems for sensing environmental conditions. More particularly, the invention relates to a microelectromechanical (MEMS) system and method for determining temperature and moisture profiles in pharmaceutical packaging.

BACKGROUND OF THE INVENTION

Pharmaceutical packaging, such as sealed pockets, blister strips, disks and packs, for doses of medicaments or pharmaceutical compositions in the form of powders, tablets or capsules are well known in the art. As applied in dry powder inhaler technology, the pharmaceutical packaging (e.g., blister strips) generally comprise a base having cavities, pockets or open "blisters" adapted to receive a pharmaceutical composition (e.g., inhalable dry powder), a lid that encloses the opening of each cavity or blister, and an adhesive or bonding layer disposed therebetween to effect a seal.

It is further well known that pharmaceutical compositions, and in particular, inhaled dry powders, must be maintained in a hermetic environment to maintain a high degree of physical stability in particle size. Only particles having a specific narrow range of aerodynamic diameter size will deposit in the desired location in the pulmonary system. For instance, a particle for local treatment of respiratory conditions such as asthma will have a particle size of 2–5 µm. Particle to particle agglomeration, shifting the particle size outside of this range, will cause the particle(s) to deposit away from the target region of the lung. Such agglomeration has been associated with moisture ingress into the pharmaceutical packaging (i.e., blister). Particle sizes, either in aerodynamic or geometric measures, referred to herein relate to a particles effective particle size. Effective particle size denotes the apparent particle size of a body without distinction as to the number of individual particles which go to make up that body, i.e., no distinction is made between the single particle of given size and an agglomerate of the same size which is composed of finer individual particles.

Similarly, exposure of a pharmaceutical composition to high temperatures can, and in many instances will, undermine the stability and, hence, efficacy of the pharmaceutical composition. Accordingly, it is important to closely monitor the environmental conditions to which a pharmaceutical composition is exposed to ensure that the pharmaceutical composition's physical and chemical stability has not been degraded.

Various prior art sensing devices and systems have been employed to monitor environmental conditions proximate pharmaceutical packaging and/or compositions. However, in general, the noted devices and systems are not suitable for monitoring environmental conditions "inside" pharmaceutical packaging, and in particular, blister packs.

For example, U.S. Pat. No. 5,739,416 discloses a surface acoustic wave (SAW) device that detects the presence of moisture. Surface acoustic waves are transmitted through a delay path that is attenuated by the presence of condensation. Unfortunately, SAW devices are extremely sensitive to temperature, pressure, and vibration or other physical conditions. Compensating for these factors increases the complexity and cost and generally renders SAW sensors unsuitable for use in pharmaceutical packaging.

There are also numerous drawbacks associated with the magnetoacoustic sensors disclosed in Jain, et al., "Magnetoacoustic remote query temperature and humidity sensors" Smart Mater. Struc. 9(2000), pp. 502–510. The most significant drawback is that the disclosed sensors are too large for incorporation into conventional pharmaceutical packaging and cannot be easily reduced in size, since size reduction substantially changes the resonant and interrogation frequencies, as well as the amplitude of the generated signal. Further, the mass changing, moisture sensitive materials disclosed by Jain, et al. would yield unsatisfactory results since they do not exhibit enough mass change when incorporated with a smaller sensor.

It is therefore an object of the present invention to provide a highly efficient, cost effective means for determining environmental conditions within a multitude of pharmaceutical packaging and, in particular, pharmaceutical packaging having limited internal space.

It is another object of the present invention to provide a microelectromechanical (MEMS) system and method for determining at least one, preferably, a plurality of environmental conditions within pharmaceutical packaging.

It is another object of the present invention to provide a remote sensor system and method for determining the temperature profile within pharmaceutical packaging.

It is another object of the present invention to provide a remote sensor system and method for determining the humidity profile within pharmaceutical packaging.

SUMMARY OF THE INVENTION

In accordance with the above objects and those that will be mentioned and will become apparent below, the sensor system for determining at least one environmental condition within pharmaceutical packaging comprises a base sheet having at least one pocket formed therein; a lid sheet having a pocket portion, the pocket portion being disposed proximate the pocket when the lid sheet is bonded to the base sheet; and a microelectromechanical (MEMS) sensor disposed proximate the pocket portion.

The invention also comprises methods for monitoring at least one environmental condition within pharmaceutical packaging. Such methods include the steps of providing at least one MEMS sensor within a packaging assembly, the sensor providing at least a first sensor signal in response to the environmental condition; and determining the environmental condition using the first sensor signal. The method may further include the steps of storing the first sensor signal, processing the first sensor signal using known algorithms and displaying the processed information. Preferably, the MEMS sensor is adapted to respond to at least one environmental condition (e.g., temperature), more preferably, humidity and temperature.

BRIEF DESCRIPTION OF THE DRAWINGS

Further features and advantages will become apparent from the following and more particular description of the preferred embodiments of the invention, as illustrated in the accompanying drawing, and in which like referenced characters generally refer to the same parts or elements throughout the views, and in which.

DETAILED DESCRIPTION OF PREFERRED EMBODIMENTS

Before describing the present invention in detail, it is to be understood that this invention is not limited to particularly exemplified systems or process parameters as such may, of course, vary. It is also to be understood that the terminology used herein is for the purpose of describing particular embodiments of the invention only, and is not intended to limit the scope of the invention in any manner.

All publications, patents and patent applications cited herein, whether supra or infra, are hereby incorporated by reference in their entirety to the same extent as if each individual publication, patent or patent application was specifically and individually indicated to be incorporated by reference.

It must be noted that, as used in this specification and the appended claims, the singular forms "a," "an" and "the" include plural referents unless the content clearly dictates otherwise. Thus, for example, reference to "a blister" includes two or more such blisters.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

In describing the present invention, the following terms will be employed, and are intended to be defined as indicated below.

Definitions

By the terms "microelectromechanical system" and "MEMS system", as used herein, it is meant to mean and include a micro-electronic and micro-mechanical systems. The systems include a device or sensor having an integrated circuit combined with a structure that responds to at least one environmental condition. Preferably, the structure is formed from the same material as the integrated circuit using micro-machining processing techniques, such as known integrated circuit fabrication techniques.

By the term "medicament", as used herein, is meant to mean and include any substance (i.e., compound or composition of matter) which, when administered to an organism (human or animal) induces a desired pharmacologic and/or physiologic effect by local and/or systemic action. The term therefore encompasses substances traditionally regarded as actives, drugs and bioactive agents, as well as biopharmaceuticals (e.g., peptides, hormones, nucleic acids, gene constructs, etc.) typically employed to treat diseases and inflammatory and respiratory disorders (e.g., asthma), including, but not limited to, analgesics, e.g., codeine, dihydromorphine, ergotamine, fentanyl or morphine; anginal preparations, e.g., diltiazem; antiallergics, e.g., cromoglycate (e.g., as the sodium salt), ketotifen or nedocromil (e.g., as the sodium salt); antiinfectives e.g., cephalosporins, penicillins, streptomycin, sulphonamides, tetracyclines and pentamidine; antihistamines, e.g., methapyrilene; anti-inflammatories, e.g., beclomethasone (e.g., as the dipropionate ester), fluticasone (e.g., as the propionate ester), flunisolide, budesonide, rofleponide, mometasone (e.g., as the furoate ester), ciclesonide, triamcinolone (e.g., as the acetonide), 6α, 9α-difluoro-11β-hydroxy-16α-methyl-3-oxo-17α-propionyloxy-androsta-1,4-diene-17β-carbothioic acid S-(2-oxo-tetrahydro-furan-3-yl) ester or 6α, 9αdifluoro-17α-[(2-furanylcarbonyl)oxy]-11β-hydroxy-16α-methyl-3-oxoandrosta-1,4-diene-17β-carbothioic acid S-fluoromethyl ester; antitussives, e.g., noscapine; bronchodilators, e.g., albuterol (e.g., as free base or sulphate), salmeterol (e.g., as xinafoate), ephedrine, adrenaline, fenoterol (e.g., as hydrobromide), formoterol (e.g., as fumarate), isoprenaline, metaproterenol, phenylephrine, phenylpropanolamine, pirbuterol (e.g., as acetate), reproterol (e.g., as hydrochloride), rimiterol, terbutaline (e.g., as sulphate), isoetharine, tulobuterol or 4-hydroxy-7-[2-[[2-[[3-(2-henylethoxy)propyl]sulfonyl]ethyl]amino]ethyl-2(3H)-benzothiazolone; PDE4 inhibitors e.g. cilomilast or roflumilast; leukotriene antagonists e.g. montelukast, pranlukast and zafirlukast; adenosine 2a agonists, e.g., (2R,3R,4S,5R)-2-[6-Amino-2-(1S-hydroxymethyl-2-phenyl-ethylamino)-purin-9-yl]-5-(2-ethyl-2H-tetrazol-5-yl)-tetrahydro-furan-3,4-diol (e.g., as maleate); $\alpha_4$ integrin inhibitors, e.g., (2S)-3-[4-({[4-(aminocarbonyl)-1-piperidinyl] carbonyl}oxy)phenyl]-2-[((2S)-4-methyl-2-{[2-(2-methylphenoxy) acetyl]amino} pentanoyl)amino] propanoic acid (e.g., as free acid or potassium salt)], diuretics, e.g., amiloride; anticholinergics, e.g., ipratropium (e.g., as bromide), tiotropium, atropine or oxitropium; ganglionic stimulants, e.g., nicotine; hormones, e.g., cortisone, hydrocortisone or prednisolone; xanthines, e.g., aminophylline, choline theophyllinate, lysine theophyllinate or theophylline; therapeutic proteins and peptides, e.g., insulin or glucagon; vaccines, diagnostics, and gene therapies. The noted medicaments may be employed in the form of salts, (e.g., as alkali metal or amine salts or as acid addition salts) or as esters (e.g., lower alkyl esters) or as solvates (e.g., hydrates) to optimize the activity and/or stability of the medicament.

The term "medicament" specifically includes albuterol, salmeterol fluticasone propionate and beclomethasone dipropionate and salts or solvates thereof e.g., the sulphate of albuterol and the xinafoate of salmeterol.

The term "medicament" further includes formulations containing combinations of active ingredients, including, but not limited to, salbutamol (e.g., as the free base or the sulfate salt) or salmeterol (e.g., as the xinafoate salt) or formoterol (e.g., as the fumarate salt) in combination with an anti-inflammatory steroid such as a beclomethasone ester (e.g., the dipropionate), a fluticasone ester (e.g., the propionate), a furoate ester or budesonide.

By the terms "medicament formulation" and "pharmaceutical composition", as used herein, it is meant to mean a combination of at least one medicament and one or more added components or elements, such as an "excipient" or "carrier." As will be appreciated by one having ordinary skill in the art, the terms "excipient" and "carrier" generally refer to substantially inert materials that are nontoxic and do not interact with other components of the composition in a deleterious manner. Examples of normally employed "excipients," include pharmaceutical grades of carbohydrates, including monosaccharides, disaccharides, cyclodextrins and polysaccharides (e.g., dextrose, sucrose, lactose, raffinose, mannitol, sorbitol, inositol, dextrins and maltodextrins); starch; cellulose; salts (e.g., sodium or calcium phosphates, calcium sulfate, magnesium sulfate); citric acid; tartaric acid; glycine; leucine; high molecular weight polyethylene glyols (PEG); pluronics; surfactants; lubricants; stearates and their salts or esters (e.g., magnesium stearate); amino acids; fatty acids; and combinations thereof.

The noted medicaments and excipients may be prepared as composite materials, such as by co-precipitation or by coating, or other method known in the art, or may be prepared from batches of separately prepared individual particles which are subsequently blended together to form particulate mixtures of medicament and excipient particles.

By the term "pharmaceutical delivery device", as used herein, it is meant to mean a device that is adapted to administer a controlled amount of a composition to a patient, including, but not limited to, the Diskus® device disclosed in U.S. Pat. No. Des. 342,994, U.S. Pat. Nos. 5,590,654, 5,860,419, 5,837,630 and 6,032,666. The term "pharmaceutical delivery device" further includes the Diskhaler™ device disclosed in U.S. Pat. No. Des 299,066; U.S. Pat. Nos. 4,627,432 and 4,811,731; the Rotahaler™ device disclosed in U.S. Pat. No. 4,778,054; the Cyclohaler™ device by Norvartis; the Turbohaler™ device by Astra Zeneca; the Twisthaler™ device by Schering Plough; the Handihaler™ device by Boehringer Ingelheim; the Airmax™ device by Baker-Norton; and the Dura and Inhaled Therapeutic active delivery systems. Each of the noted "pharmaceutical delivery devices" are incorporated by reference herein.

By the terms "pharmaceutical packaging" and "packaging", as used herein, it is meant to mean conventional pharmaceutical containment systems and packaging having at least one sealable pocket, cavity or blister adapted to contain at least one medicament or a pharmaceutical composition in any conventional form, including a powder, capsule or tablet. The terms "pharmaceutical packaging" and "packaging" thus include conventional blister strips, disks (e.g., Rotadisk™), packs, sheets and individual containers that are employed in the aforementioned "pharmaceutical delivery devices", including, but not limited to, the pharmaceutical packaging disclosed in U.S. Pat. Nos. 6,032,666, 6,155,423 and 4,778,054.

As will be appreciated by one having ordinary skill in the art, the present invention substantially reduces or eliminates the disadvantages and drawbacks associated with conventional sensor systems and methods for monitoring environmental conditions. As discussed in detail below, the microelectromechanical (MEMS) sensors of the invention can readily be disposed proximate to or in one or more blisters of a blister strip pack, disk or sheet to determine temperature and moisture profiles proximate a pharmaceutical composition sealed therein. The MEMS sensors of the invention can also be readily incorporated in individual containers, such as a vial.

Figure 1:
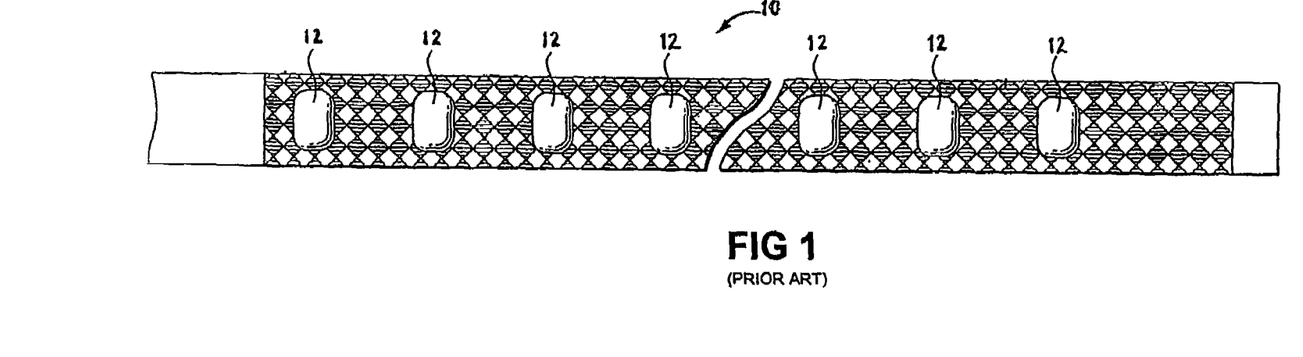
FIG. 1 is a top plan view of a prior art blister strip.
Figure 2:
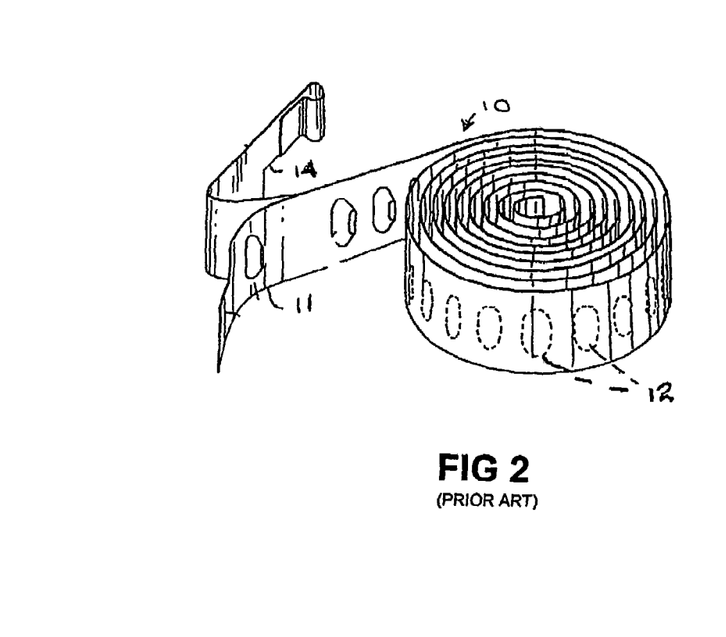
FIG. 2 is a perspective view of a prior art blister strip.
Figure 4:
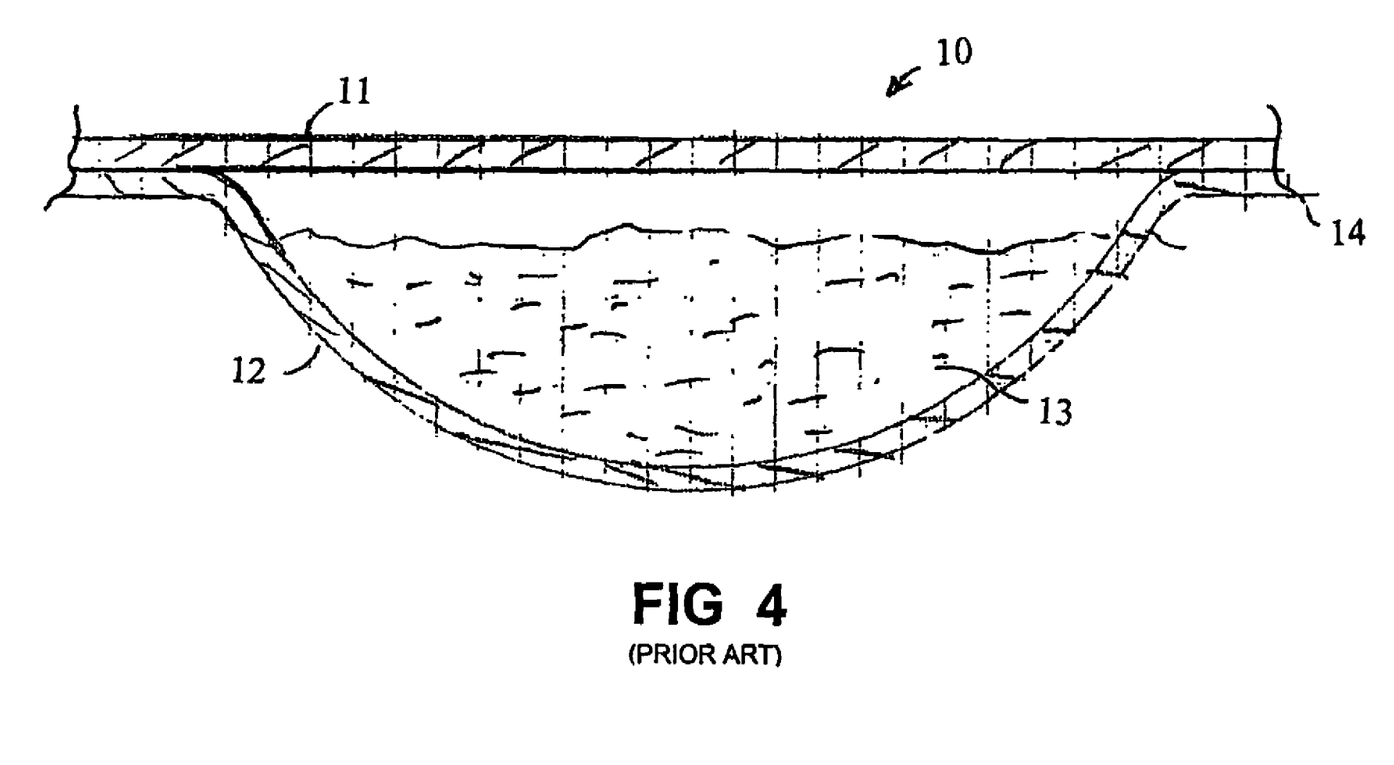
FIG. 4 a partial section view of a prior art blister containing a pharmaceutical composition.

Referring first to FIGS. 1 and 2, there is shown conventional pharmaceutical packaging in the form of a blister strip 10. As illustrated in FIGS. 1 and 4, the blister strip 10 includes a lid 11 and a base 14 having a plurality of blisters 12 formed therein adapted to receive a pharmaceutical composition 13, preferably in the form of a dry powder. Each blister 12 typically has a length in the range of 1.5 to 8.0 mm and a width in the range of 1.5 to 8.0 mm. More typically, the width is approximately 4.0 mm.

Figure 3:
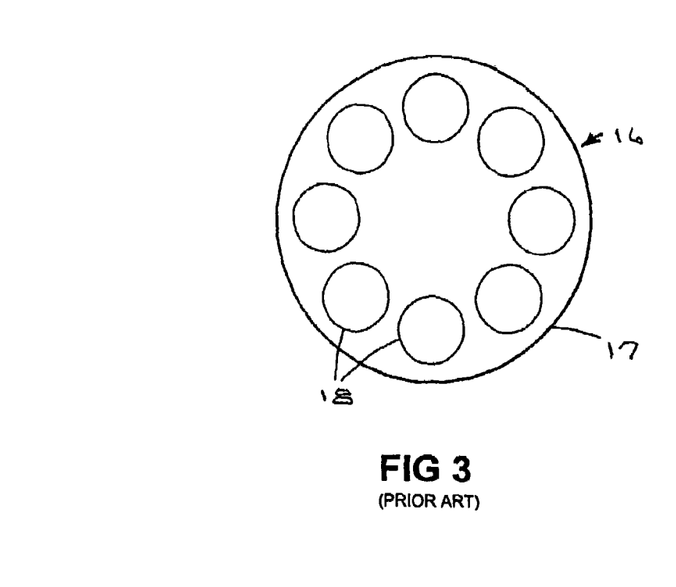
FIG. 3 is a top plan view of a prior art blister pack.

Referring now to FIG. 3, there is shown further prior art pharmaceutical packaging in the form of a blister pack 16. The blister pack 16 similarly includes a lid (not shown) and a base 17 having a plurality of blisters 18 formed therein adapted to receive a pharmaceutical composition 13.

According to the invention, the MEMS sensors (and systems) of the invention are characterized by combining conventional integrated circuits with mechanical components fabricated from the integrated circuit materials. As discussed below, in one embodiment, the MEMS sensor 21 includes a vapor sensing element 24 having a moisture sensitive coating (e.g., polymer) 26 that is shear constrained (see FIG. 6B). According to the invention, the adsorption of water vapor generates shear stress that is measured via an embedded strain gauge. The MEMS sensor is also adapted to respond to changes in temperature (e.g., piezoresistive temperature sensing element). Suitable MEMS sensors of this type include the HMX2000™ sensor available from Hygrometrix (Alpine, Calif.).

Figure 5A:
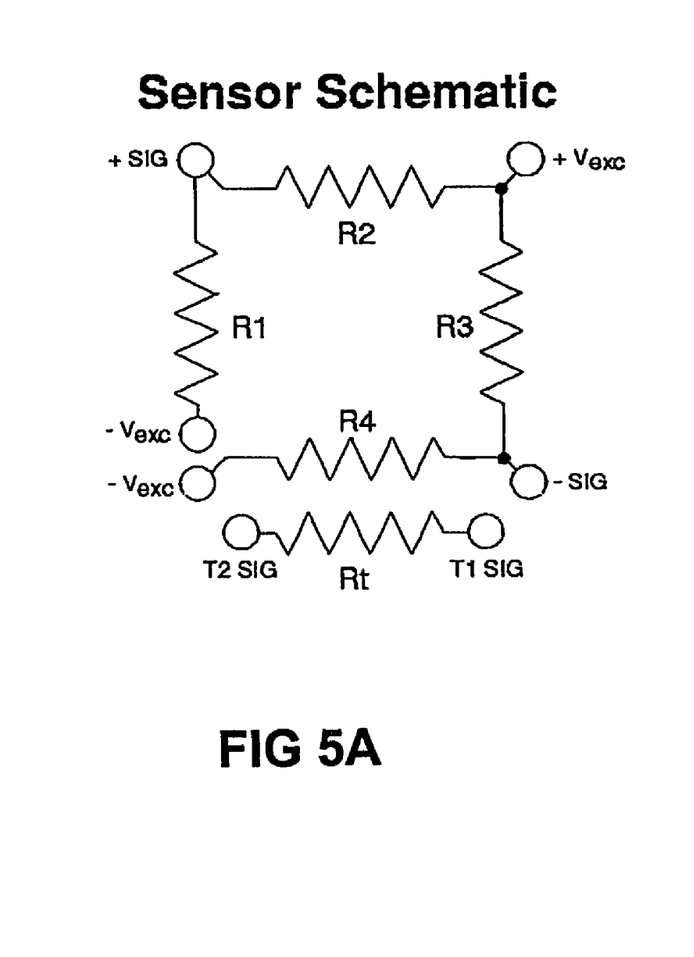
FIG. 5A is a schematic illustration of one embodiment of a microelectromechanical sensor, according to the invention.
Figure 5B:
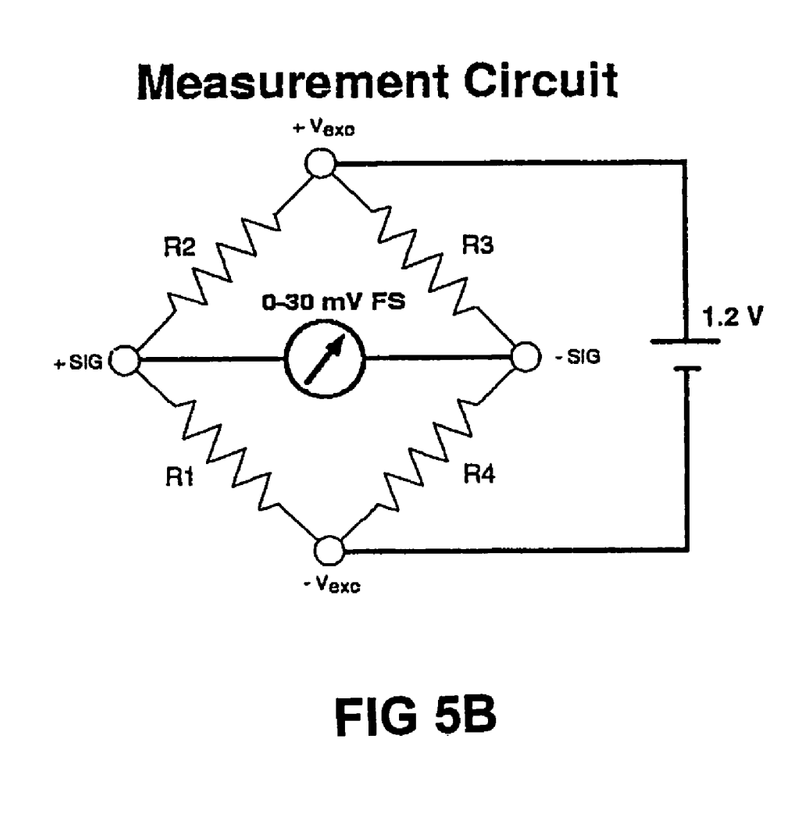
FIG. 5B is a schematic illustration of a microelectromechanical sensor measurement circuit, according to the invention.

In the noted embodiment, the vapor sensing element is constructed from a thin polymer film deposited and bonded to the top surface of four cantilever beams that are machined from the surrounding silicon substrate using integrated circuit techniques. The shear/stress force generated in the thermoset polymer coating measures the physical van der Waals forces as resistance change. Referring to FIGS. 5A and 5B, a Wheatstone Bridge piezoresistor circuit delivers a DC output voltage that is linearly proportional to relative humidity ("RH"). Further details of the noted MEMS system are set forth in U.S. Pat. No. 5,563,341, which is hereby incorporated by reference in its entirety.

Another suitable MEMS system is disclosed in Wachter, et. al., "Micromechanical Sensors for Chemical and Physical Measurements", Rev. Sci. Instrum., 66(6), June 1995. The noted MEMS system comprises a relative humidity sensor that utilizes a micro-cantilever beam with a sorption coating of gelatin for measuring humidity. The moisture sensitive coating changes mass as differing amounts of water vapor are adsorbed at different humidity levels. Since the mass affects the resonant frequency of the cantilever beam, measuring the frequency allows the corresponding humidity to be determined.

Yet another suitable MEMS system is disclosed in U.S. Pat. No. 6,128,961, which is hereby incorporated by reference. The noted MEMS system relies on the direct integration of a single crystal silicon device with sensing elements, such as Schottky and junction diodes, piezoresistors, bipolar and MOSFET transistors. The system utilizes mechanical deformation of a sensing element to modulate its electrical properties.

As will be appreciated by one having ordinary skill in the art, various additional, conventional MEMS systems can be employed within the scope of the invention. Such MEMS systems include the thermo-mechanical sensor disclosed in U.S. Pat. No. 5,917,226 and the MEMS system disclosed in U.S. Pat. No. 6,255,962, which are similarly incorporated by reference herein.

Figure 6A:
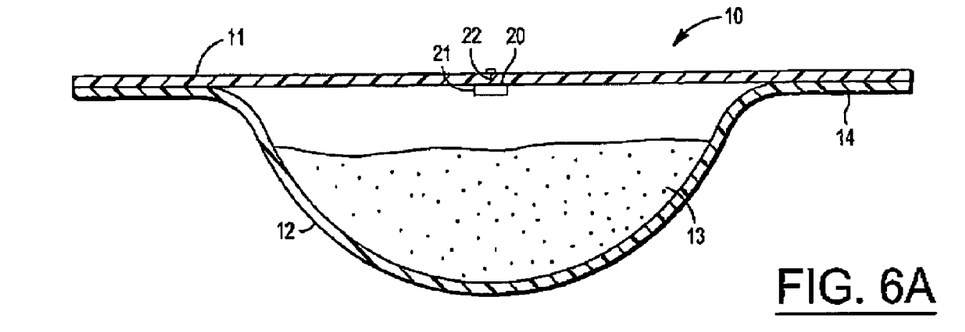
FIG. 6A is a partial section view of one embodiment of a microelectromechanical sensor system, according to the invention.
Figure 6B:
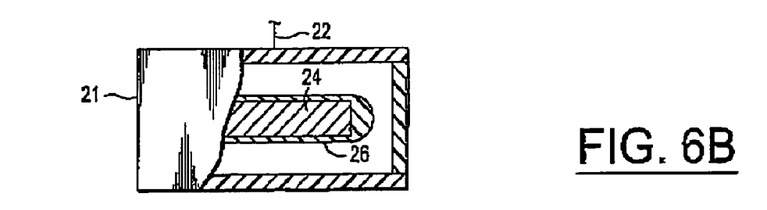
FIG. 6B is a partial section view of one embodiment of a microelectromechanical sensor, illustrating a cantilevered sensing element, according to the invention.

Referring now to FIG. 6, there is shown a "packaging assembly", incorporating a MEMS system 20 of the invention. In the noted "packaging assembly" embodiment, at least one MEMS sensor (or system) 21 is preferably attached to the lid 11 of the pharmaceutical packaging or blister pack 10 prior to sealably bonding the lid 11 to the base 14. As illustrated in FIG. 6, the sensor 21 includes the aforementioned sensing element 24, which in one embodiment comprises a cantilever beam, having a moisture sensitive coating 26 thereon, and a lead 21 that extends outside the blister pack 10.

Preferably, the sensor 21 is positioned on the lid 11 such that after bonding the lid 11 to the base 14, the sensor 21 is disposed proximate, preferably, immediately above, the blister 12. In additional envisioned embodiments of the invention, not shown, the sensor 21 is suitably attached to the base 14 proximate to or within a respective blister 12.

The MEMS sensor is preferably adapted to respond to at least one environmental condition (e.g., temperature), more preferably, a plurality of environmental conditions. Even more preferably, the MEMS sensor is adapted to respond to temperature and humidity (i.e., provide sensor signals representative of detected temperature and humidity data).

Figure 7:
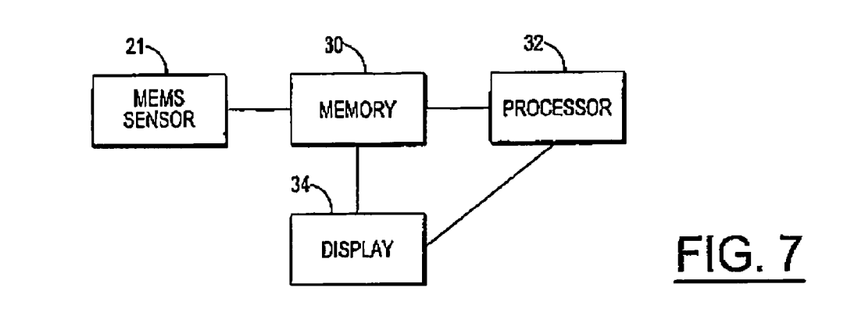
FIG. 7 is a schematic illustration of a further embodiment of a microelectromechanical sensor system, according to the invention.

Referring now to FIG. 7, in a preferred embodiment, the MEMS system 20 further includes a memory 30 in communication with the MEMS sensor 21 for storing sensor signals representative of sensed data, a low power, data acquisition processor 32 for processing the sensor signals and a display 34.

Preferably, the processor 32 contains the necessary circuitry to amplify and process sensor signals to a value corresponding to the measured temperature, humidity or other environmental condition. According to the invention, the display 34 may comprise an alphanumeric display that communicates at least stored sensor signals and/or calculated values reflecting measured environmental conditions. Alternatively, the display 34 may simply comprise an audio or visual indication of whether a particular threshold condition has been monitored, such as whether the environment in the packaging has experienced a predetermined temperature or humidity.

In additional envisioned embodiments, the circuitry necessary to perform the processing and memory functions of the invention is incorporated into the integrated circuitry of the MEMS sensor 21.

The present invention also includes a method for monitoring temperature and humidity inside pharmaceutical packaging. The method preferably includes collecting a plurality of sensor signals representative of sensed data from at least one MEMS sensor, more preferably, at least a plurality of MEMS sensors, i.e., MEMS 1, MEMS 2. The plurality of MEMS sensors preferably generate sensed data representative of at least temperature and/or humidity.

The method also includes converting the plurality of sensor signals into digital data, processing the digital data, and simultaneously and remotely detecting the processed data to determine the occurrence of at least one predetermined condition.

The method can also advantageously include remotely communicating the processed digital data. The step of remotely communicating the processed digital data preferably includes transmitting the processed digital data by the use of a RF transmitter and receiving the transmitted RF data prior to the step of simultaneously and remotely detecting.

The method additionally can include storing the processed digital data until remotely accessed, storing the unprocessed digital data until remotely accessed and displaying processed and unprocessed digital data after being remotely accessed, operatively sampling the plurality of sensors and analyzing the processed digital data at predetermined scripted real time intervals, and operatively generating a data report and generating an alarm condition when predetermined threshold conditions occur.

The method can further advantageously include generating a data communications protocol having the processed digital data and communicating the data communications protocol having the processed digital data responsive to remote access.

Without departing from the spirit and scope of this invention, one of ordinary skill can make various changes and modifications to the invention to adapt it to various usages and conditions. In particular, the invention has been described primarily in reference to the determination of temperature and humidity within pharmaceutical packaging. However, the invention may be applied to remotely determine any suitable environmental condition within any package, container or other enclosed space. As such, these changes and modifications are properly, equitably, and intended to be, within the full range of equivalence of the following claims.

What is claimed is:

1. A sensor system for determining an environmental condition within pharmaceutical packaging, comprising:
   a base sheet having at least one pocket formed therein;
   a lid sheet, said lid sheet including a pocket portion, said pocket portion being disposed proximate said pocket when said lid sheet is bonded to said base sheet, said lid sheet and said base sheet forming an internal cavity when said lid sheet is bonded to said base sheet; and
   a microelectromechanical sensor disposed proximate said pocket portion, said sensor including a sensing element having a moisture sensitive coating thereon, said sensor providing at least first sensor signal in response to an environmental condition within said internal cavity.

2. A sensor system for determining an environmental condition within pharmaceutical packaging, comprising:
   a base sheet having at least one pocket formed therein;
   a lid sheet, said lid sheet including a pocket portion, said pocket portion being disposed proximate said pocket when said lid sheet is bonded to said base sheet, said lid sheet and said base sheet forming an internal cavity when said lid sheet is bonded to said base sheet; and
   a microelectromechanical sensor disposed proximate said pocket portion, said sensor including a sensing element having a moisture sensitive coating thereon, said moisture sensitive coating changing mass with changes in relative humidity, said sensor providing at least first sensor signal in response to an environmental condition within said internal cavity.

3. A said sensor system for determining an environmental condition within pharmaceutical packaging, comprising:
   a base sheet having at least one pocket formed therein;
   a lid sheet, said lid sheet including a pocket portion, said pocket portion being disposed proximate said pocket when said lid sheet is bonded to said base sheet, said lid sheet and said base sheet forming an internal cavity when said lid sheet is bonded to said base sheet; and
   a microelectromechanical sensor disposed proximate said pocket portion, said sensor including a sensing element having a moisture sensitive coating thereon, said sensing element comprising a cantilever beam, said sensor providing at least first sensor signal in response to an environmental condition within said internal cavity.

4. A sensor system for determining an environmental condition within pharmaceutical packaging comprising:
- a base sheet having at least one pocket formed therein;
- a lid sheet, said lid sheet including a pocket portion, said pocket portion being disposed proximate said pocket when said lid sheet is bonded to said base sheet, said lid sheet and said base sheet forming an internal cavity when said lid sheet is bonded to said base sheet; and
- a microelectromechanical sensor disposed proximate said pocket portion, said sensor including a sensing element having a moisture sensitive coating thereon, said sensing element comprising a cantilever beam, said sensor providing at least first sensor signal in response to an environmental condition within said internal cavity,
- wherein adsorption of water vapor by said moisture sensitive coating produces a shear stress at the interface of said sensing element and said moisture sensitive coating, and wherein said moisture sensitive coating is shear restrained by said sensing element.

5. A sensor system for determining an environmental condition within pharmaceutical packaging, comprising:
- a base sheet having at least one pocket formed therein;
- a lid sheet, said lid sheet including a pocket portion, said pocket portion being disposed proximate said pocket when said lid sheet is bonded to said base sheet, said lid sheet and said base sheet forming an internal cavity when said lid sheet is bonded to said base sheet;
- a microelectromechanical sensor disposed proximate said pocket portion, said sensor including a sensing element having a moisture sensitive coating thereon, said moisture sensitive coating changing mass with changes in relative humidity, said sensor providing at least first sensor signal in response to an environmental condition within said internal cavity;
- a memory adapted to receive and store said first sensor signal;
- a processor for determining at least said environmental condition using said first sensor signal; and
- a display in communication with said processor for displaying at least said environmental condition.

* * * * *